(12) United States Patent
Waldmann-Laue et al.

(10) Patent No.: US 6,419,937 B1
(45) Date of Patent: Jul. 16, 2002

(54) LIPOPROTEIN CREAMS

(75) Inventors: Marianne Waldmann-Laue, Monheim; Thomas Foerster, Erkrath; Soraya Heinen, Cologne; Leszek Bialasinski, Ratingen; Karlheinz Schrader, Bevern, all of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/600,451

(22) PCT Filed: Jan. 9, 1999

(86) PCT No.: PCT/EP99/00085

§ 371 (c)(1),
(2), (4) Date: Sep. 5, 2000

(87) PCT Pub. No.: WO99/36051

PCT Pub. Date: Jul. 22, 1999

(30) Foreign Application Priority Data

Jan. 17, 1998 (DE) .......................... 198 01 593

(51) Int. Cl.[7] .......................... A61K 7/00; A61K 7/48; A61K 9/127; A61K 9/107

(52) U.S. Cl. .................. 424/401; 424/78.03; 424/70.1; 424/450; 514/785

(58) Field of Search .............................. 424/401, 78.03, 424/450; 514/785; 106/126

(56) References Cited

U.S. PATENT DOCUMENTS

| | | | | |
|---|---|---|---|---|
| 4,360,537 A | | 11/1982 | Tan et al. ................... 426/656 |
| 4,719,239 A | * | 1/1988 | Muller et al. ................ 514/785 |
| 5,322,839 A | | 6/1994 | Voegeli et al. ................ 514/21 |
| 5,525,151 A | * | 6/1996 | Lenz et al. .................. 106/126 |
| 6,132,738 A | * | 3/1998 | Lerg et al. .................. 424/401 |
| 5,908,618 A | * | 6/1999 | Lorant ........................ 424/70.5 |

FOREIGN PATENT DOCUMENTS

| | | | |
|---|---|---|---|
| DE | 19712678 A1 | * | 1/1998 |
| EP | 0 371 601 | | 6/1990 |
| EP | 0 532 465 | | 3/1993 |
| EP | 0 620 979 | | 10/1994 |
| WO | WO 90/05521 | | 5/1990 |
| WO | WO 94/18944 | | 9/1994 |
| WO | WO 94/21222 | | 9/1994 |
| WO | WO 95/11663 | | 5/1995 |

* cited by examiner

*Primary Examiner*—Jose' G. Dees
*Assistant Examiner*—Mina Haghighatian
(74) *Attorney, Agent, or Firm*—Stephen D. Harper; Kimberly R. Hild; Glenn E. J. Murphy

(57) ABSTRACT

The invention relates to cosmetic and pharmaceutical creams in the form of an oil-in-water emulsion containing at least one polar oil as the oil component, said polar oil having an interfacial tension ($\gamma^1$) with water of less than 30 mN/m at 25° C., and at least one plant protein as the emulsifier, a 1 wt % aqueous solution of said plant protein having an interfacial tension ($\gamma^2$) with the oil component at 25° C. which is less than the interfacial tension $\gamma^1$ between oil and water. Protein or protein-containing meals consisting of oats, wheat or peas are preferred as emulsifiers, whilst the oil components preferably belong to the group of $C_8$–$C_{22}$ fatty acid esters of monovalent or polyvalent $C_2$–$C_{22}$ alkanol esters of monovalent or polyvalent $C_2$–$C_6$ hydroxycarboxylic acids.

12 Claims, No Drawings

LIPOPROTEIN CREAMS

CROSS REFERENCE TO RELATED APPLICATIONS

This application is national stage application under 35 U.S.C. §371 of international application PCT/EP99/00085 filed on Jan. 9, 1999, the international application not being published in English.

BACKGROUND OF THE INVENTION

This invention relates to cosmetic and pharmaceutical creams in the form of oil-in-water emulsions of polar oil components which contain vegetable proteins or protein-rich flours of plant seed kernels as emulsifiers. The creams according to the invention may be formulated without the use of the usual ionic or hydrophilic, nonionic emulsifiers and, accordingly, have a particularly good skin care effect.

The use of soya protein in combination with typical ethoxylated emulsifiers and phospholipids for the production of lipoprotein emulsions, for example for the food and confectionery industry, is known from U.S. Pat. No. 4,360,537. Proteins have also been repeatedly described as emulsifiers for cosmetic emulsions. Thus, it is known from WO 94/21222 A1 that protein-containing flours of plant seeds can be used as emulsifiers for sun protection lotions. Unfortunately, emulsions such as these are very limited in their stability unless they additionally contain hydrophilic emulsifiers.

The present invention is based on the observation that certain vegetable proteins in the form of aqueous solutions reduce not only the surface tension of water, i.e. the water/air interfacial tension, but also the interfacial tension between water and an adjoining oil phase. If the oil phase has a certain polarity, i.e. if the water/oil interfacial tension is below 30 mN/m (25° C.), highly stable oil-in-water emulsions can be produced with protein preparations such as these. Accordingly, the problem addressed by the present invention was to provide suitable protein preparations and correspondingly adapted oil components which, by virtue of their interfacial properties, would enable stable emulsions to be prepared without any need for typical o/w emulsifiers. By virtue of their lipophilic properties, the vegetable proteins suitable for this purpose are also referred to hereinafter as lipoproteins.

DESCRIPTION OF THE INVENTION

The present invention relates to cosmetic and pharmaceutical creams in the form of an oil-in-water emulsion which contain as oil components at least one polar oil of which the interfacial tension with water at 25° C. ($\gamma^1$) is below 30 mN/m (millinewtons per liter) and which contains as emulsifier at least one vegetable protein of which a 1% by weight aqueous solution (or dispersion) has an interfacial tension with the oil component at 25° C. ($\gamma^2$) which is lower than the interfacial tension $\gamma^1$ between oil and water.

Cosmetic creams in the context of the present invention are understood to be compositions which, through the presence of the oil component and the active substances dissolved therein or in the aqueous phase, have a cosmetic effect on the skin or hair. Thus, certain oil components have a skin-softening effect. Suitable oil-soluble cosmetic active principles are, for example, ceramides or ceramide analogs, vitamins, for example tocopherols or tocopherol esters, retinol esters, for example retinol palmitate, sterols, bisabolol, perfumes, oil-soluble sun protection factors, sebostatic agents and other substances which improve the sensorial properties of the skin or the hair or which protect the skin or the hair. Suitable water-soluble cosmetic active principles are, for example, urea, allantoin, water-soluble vitamins (ascorbic acid), magnesium salts, sugars and polyols such as, for example, glycerol, sorbitol or propylene glycol and water-soluble plant extracts. Finally, the water-soluble proteins themselves have a cosmetically favorable effect on the skin by leading to the formation of non-fatting lipoprotein films on the skin with a high water retention capacity.

In addition, the creams according to the invention may also contain oil-soluble or water-soluble pharmaceutical or dermatological active principles for treating diseases of the skin or scalp.

Particularly suitable oil components are oils or mixtures of oils which have an interfacial tension ($\gamma^1$) with water at 25° C. of 5 to 20 mN/m and preferably in the range from 6 to 15 mN/m, i.e. oils with a medium to relatively high polarity.

Suitable oil components are those containing an ester group in the molecule, for example the fatty acid esters of monohydric $C_{2-18}$ alcohols such as, for example, ethyl stearate, isopropyl stearate, isopropyl myristate, butyl stearate, hexyl laurate or stearyl isononanoate and also dicarboxylic acid esters such as, for example, di-n-butyl adipate or diisooctyl succinate.

Preferred oil components are one or more from the group of $C_{8-22}$ fatty acid esters of monohydric or polyhydric $C_{2-6}$ alcohols or $C_{12-22}$ alcohol esters of monobasic or polybasic $C_{2-6}$ hydroxycarboxylic acids or mixtures thereof.

Suitable $C_{8-22}$ fatty acid esters of polyhydric $C_{2-6}$ alcohols are, for example, the fatty acid triglyceride oils occurring as vegetable and animal oils, for example olive oil, sunflower oil, soybean oil, sesame oil, hazel nut oil, almond oil, thistle oil. A less suitable oil is, for example, evening primrose oil, of which the polarity is so high that it has a considerable interfacial activity of its own (see Example 07 on page 7). Other suitable esters of this type are the fatty acid esters of 1,2-propylene glycol, neopentyl glycol, trimethylol propane and pentaerythritol.

Suitable $C_{8-22}$ fatty alcohol esters of monobasic or polybasic hydroxycarboxylic acids are, above all, the esters of glycolic acid, lactic acid, malic acid, tartaric acid and citric acid.

Corresponding esters based on linear $C_{14/15}$ alkanols and $C_{12/13}$ alkanols branched in the 2-position are commercially obtainable under the name of Cosmacol®-Ester (manufacturer: Eni Chem. Augusta Industriale) from Nordmann, Rassmann GmbH & Co., Hamburg. Not only are these esters particularly suitable for the production of the lipoproteins creams according to the invention, they also have other highly desirable skin-care effects, for example they accelerate cell renewal and slow down ageing of the skin.

The creams according to the invention contain as emulsifier an interfacially active vegetable protein (lipoprotein) which, in the form of a 1% by weight solution in water, reduces the interfacial tension between the oil component and water. Preferred vegetable proteins are those which, in the form of a 1% by weight solution, reduce the interfacial tension between water and the oil component at 25° C. by an amount ($\gamma^1-\gamma^2$) of at least 2 mN/m.

Proteins from oats, peas, soya and wheat above all have proved to be suitable vegetable proteins which satisfy these requirements in the case of the oil components suitable for use in accordance with the invention. However, it may be assumed that many proteins from plant seeds, for example almond protein, hazel nut protein and, above all, cereal proteins are equally suitable.

The proteins suitable for use in accordance with the invention may differ in their purity. However, the protein content should be at least 10% by weight or more. Processes for purifying and isolating vegetable proteins are widely described in the patent literature. For example EP 620 979 A1 describes a process for the production of low-fat oat protein solutions. EP 371 601 A2 describes another process for isolating a surfactant-like protein fraction from oats. A process for the production of a protein concentrate containing 10 to 20% by weight protein by extraction of lipidic impurities with hexane is described in WO 94/21222 A1.

The protein suitable for use in accordance with the invention does not have to form a clear solution in water. Instead, it is entirely sufficient for the protein to dissolve in water at 25° C. in such a quantity that the content of dissolved protein reduces the interfacial tension with the oil component present by at least 2 mN/m in relation to pure water. The content of water-soluble protein or protein dissolved in water is normally at least 0.1% by weight of the aqueous phase.

Around 1 to 10% by weight of the protein or protein-containing flour, based on the cream according to the invention, are preferably used. The oil components are preferably present in the cream according to the invention in a quantity of 1 to 20% by weight.

The lipoprotein creams according to the invention may contain typical galenic auxiliaries in the usual quantities as further auxiliaries. Examples of auxiliaries such as these are thickeners for the aqueous phase, for example vegetable gums, water-soluble cellulose ethers, water-soluble biopolymers and water-soluble synthetic polymers, layer silicates and pyrogenic silicas. Other suitable auxiliaries are, for example, polyols or glycols such as, for example, glycerol, 1,2-propylene glycol, 1,3-butylene glycol or sorbitol, preservatives such as, for example, pentane-1,5-diol, phenoxyethanol, p-hydroxybenzoic acid ester, glycine or sorbic acid, complexing agents (for example Trilon B), antioxidants and dyes and perfumes.

Although often not necessary, it can be of advantage additionally to use co-emulsifiers selected from polar fatty compounds or water-in-oil emulsifiers to increase the stability of the emulsions. Preferred co-emulsifiers are those from the group of $C_{12-22}$ fatty alcohols, for example cetyl/stearyl alcohol, or $C_{12-22}$ fatty acid partial esters of $C_{2-6}$ polyols used in a quantity of 0.1 to 1 part by weight per part by weight of the oil component.

By contrast, water-soluble surfactants or emulsifiers of the o/w type are not necessary for stabilizing the creams according to the invention which, in a preferred embodiment, are substantially free from ionic and hydrophilic emulsifiers with an HLB value of 5 or more.

The following Examples are intended to illustrate the invention without limiting it in any way.

EXAMPLES

1. Investigation of the Interfacial Tension Between Oil Components and Water or 1% by Weight Solutions of Proteins in Water The following commercial products were used:

| Protein preparations: | |
|---|---|
| P1 : Tech-O-6-020 MC | hydrolyzed oat protein |
| P2 : COS-152-11-A | oat protein |
| P3 : COS-152-15-A | wheat protein |
| P4 : Tech-O-6-40-L | oat protein extract |
| P5 : COS-151-2-A | pea protein |
| P6 : Tech-O-11-070 | oatmeal (ca. 13% by weight protein) |
| Oil components: | |
| Myritol ® PC | propylene glycol dicaprylate/dicaprate |
| Kessco ® IPS | isopropyl stearate |
| IPIS | isopropyl isostearate |
| Cetiol ® MM | myristyl myristate |
| Mixed oil component: | |
| Cosmacol ® PLG | mixture of di-$C_{12-13}$ alkyl tartrate, tri-$C_{12-13}$-alkyl citrate and silica |

Composition of other oil components (in parts by weight)

| | 01 | 02 | 03 | 04 | 05 | 06 | 07 | 08 |
|---|---|---|---|---|---|---|---|---|
| Myritol PC | 1 | 1 | 1 | 1 | 1 | 1 | 1 | 1 |
| Kessco IPS | 2 | 2 | — | 2 | 2 | 2 | 2 | 1 |
| IPIS | — | — | 2 | — | — | — | — | — |
| Cosmacol PLG | 1 | 1 | 1 | 1 | 1 | 1 | 1 | 1 |
| Thistle oil | — | 1 | 1 | — | — | — | — | — |
| Almond oil | — | — | — | 1 | — | — | — | — |
| Sesame oil | — | — | — | — | 1 | — | — | — |
| Castor oil | — | — | — | — | — | 1 | — | — |
| Evening primrose oil | — | — | — | — | — | — | 1 | — |

Measurement of interfacial tension:

Interfacial tension (mN/m) 25° C.

| Oil component | Water ($\gamma^1$) | 1% by weight protein in water ($\gamma^2$) |
|---|---|---|
| Kessco IPS | 27.8 | 17.7 (protein P1) |
| | | 15.5 (protein P2) |
| | | 15.8 (protein P3) |
| | | 20.7 (protein P4) |
| | | 11.4 (protein P5) |
| | | 19.2 (protein P6) |
| 01 | 7.1 | 3.8 (protein P6) |
| 02 | 10.8 | 5.1 (protein P6) |
| 03 | 10.9 | 4.4 (protein P6) |
| 04 | 10.4 | 3.9 (protein P6) |
| 05 | 10.8 | 4.1 (protein P6) |
| 06 | 14.1 | 5.9 (protein P6) |
| 07 | 4.5 | 4.7 (protein P6) |
| 08 | 24.8 | Protein P1 : 14.0 |
| | | Protein P2 : 15.3 |
| | | Protein P3 : 13.4 |
| | | Protein P4 : 18.6 |
| | | Protein P5 : 8.9 |
| | | Protein P6 : 9.4 |

The measurements were carried out using a ring tensiometer.

2. Examples of Creams According to the Invention (1–8)

| | |
|---|---|
| Oil component 01 to 08 | 3.0% by weight |
| Myritol PC | 3.5% by weight |
| Kessco IPS | 6.0% by weight |
| Cosmacol PLG | 3.0% by weight |
| Cetiol MM | 2.5% by weight |
| Cutina MD-A | 2.5% by weight |
| Stenol 16/18 | 2.0% by weight |
| Crodamol PMP | 1.0% by weight |
| Protein P6 or P5 | 3.0% by weight |
| 1,3-Butylene glycol | 10.0% by weight |
| Glycine | 1.0% by weight |
| Trilon B (EDTA) | 0.2% by weight |
| Water | Balance to 100% |

The following co-emulsifiers were used:

| | |
|---|---|
| (1) Cutina ® MD-A | glycerol mono-/di-palmitate/stearate |
| (2) Stenol ® 1618 | cetyl/stearyl alcohol (1:2) |
| (3) Crodamol ® PMP | PPG-2-myristyl ether propionate |

Production

The protein preparation was dissolved (or swollen) in water heated to 60–80° C. using a homogenizer (Ultraturax). The swollen/dissolved protein was then combined while stirring with the water phase heated to 60–80° C. (water, 1,3-butylene glycol, glycine, Trilon B).

The oil components and co-emulsifiers were mixed and heated to around 80° C. Finally, the oil phase was combined with the hot water phase and emulsified.

A stable emulsion was formed, changing into a smooth highly stable cream after cooling to 20° C. The cream formed with oil component 07 was unstable.

What is claimed is:

1. A cosmetic or pharmaceutical cream in the form of an oil-in-water emulsion, comprising as an oil component at least one polar oil, of which the interfacial tension with water at 25° C. ($\gamma^1$) is below 30 mN/m, and as an emulsifier component at least one vegetable protein of which a 1% by weight aqueous solution has an interfacial tension with the oil component at 25° C. ($\gamma^2$) that is lower than the interfacial tension ($\gamma^1$), the cosmetic or pharmaceutical cream being free of ionic and hydrophilic emulsifiers having HLB values of 5 or more.

2. The cosmetic or pharmaceutical cream of claim 1, wherein the polar oil component comprises an oil or a mixture of oils having an interfacial tension ($\gamma^1$) with water at 25° C. in the range of 5 to 20 mN/m.

3. The cosmetic or pharmaceutical cream of claim 2, wherein the polar oil component comprises an oil or a mixture of oils having an interfacial tension ($\gamma^1$) with water at 25° C. in the range of 6 to 15 mN/m.

4. The cosmetic or pharmaceutical cream of claim 1, wherein the emulsifier component reduces the interfacial tension between water and the oil component at 25° C. by an amount ($\gamma^1$)–($\gamma^2$) of at least 2 mN/m.

5. The cosmetic or pharmaceutical cream of claim 1, wherein the vegetable protein comprises a protein from oats, wheat, or peas, or a protein-rich flour from plant seeds comprising more than 10% by weight protein.

6. The cosmetic or pharmaceutical cream of claim 2, wherein the vegetable protein comprises a protein from oats, wheat, or peas, or a protein-rich flour plant seeds comprising more than 10% by weight protein.

7. The cosmetic or pharmaceutical cream of claim 4, wherein the vegetable protein comprises a protein from oats, wheat, or peas, or a protein-rich flour from plant seeds comprising more than 10% by weight protein.

8. The cosmetic or pharmaceutical cream of claim 1, wherein the oil component comprises one or more compounds selected from $C_{8-22}$ fatty acid esters of monohydric or polyhydric $C_{2-6}$ alcohols, or $C_{12-22}$ alkanol esters of monobasic or polybasic $C_{2-6}$ hydroxycarboxylic acids.

9. The cosmetic or pharmaceutical cream of claim 1, comprising one or more co-emulsifiers selected from $C_{12-22}$ fatty alcohols, or $C_{12-22}$ fatty acid partial esters of $C_{2-6}$ polyols in a quantity of 0.1 to 1 part by weight per part by weight of the oil component.

10. The cosmetic or pharmaceutical cream of claim 1 wherein the cream is a skin-care composition.

11. The cosmetic or pharmaceutical cream of claim 1 wherein the oil component is present in an amount of 1 weight percent to 20 weight percent, based on th total weight of the composition.

12. The cosmetic or pharmaceutical cream of claim 1 wherein the vegetable protein is present in an amount of from about 1 weight percent to about 10 weight percent, based on the total weight of the composition.

* * * * *

UNITED STATES PATENT AND TRADEMARK OFFICE
CERTIFICATE OF CORRECTION

PATENT NO. : 6,419,937 B1  Page 1 of 1
DATED : July 16, 2002
INVENTOR(S) : Waldmann-Laue et al.

It is certified that error appears in the above-identified patent and that said Letters Patent is hereby corrected as shown below:

Title page,
Item [57], ABSTRACT,
Line 9, after "water.", delete "Protein", and insert therefor -- Proteins --.
Line 12, after "polyvalent", delete "$C_2$-$C_{22}$", and insert therefor -- $C_2$-$C_6$ alkanols or $C_8$-$C_{22}$ --.

Column 6,
Line 39, delete "th", and insert therefor -- the --.

Signed and Sealed this

Thirteenth Day of January, 2004

JON W. DUDAS
*Acting Director of the United States Patent and Trademark Office*